United States Patent
Falahee

(10) Patent No.: US 9,089,373 B2
(45) Date of Patent: Jul. 28, 2015

(54) SPINOUS PROCESS RETRACTOR

(75) Inventor: Mark H. Falahee, Ann Arbor, MI (US)

(73) Assignee: Medical Design Instruments, LLC, Ann Arbor, MI (US)

(*) Notice: Subject to any disclaimer, the term of this patent is extended or adjusted under 35 U.S.C. 154(b) by 569 days.

(21) Appl. No.: 12/696,419

(22) Filed: Jan. 29, 2010

(65) Prior Publication Data

US 2010/0241128 A1 Sep. 23, 2010

Related U.S. Application Data

(60) Provisional application No. 61/162,416, filed on Mar. 23, 2009.

(51) Int. Cl.
*A61B 17/58* (2006.01)
*A61B 17/60* (2006.01)
*A61F 2/00* (2006.01)
*A61B 17/70* (2006.01)
*A61B 17/02* (2006.01)
*A61B 17/28* (2006.01)
*A61B 17/88* (2006.01)

(52) U.S. Cl.
CPC ........... *A61B 17/7074* (2013.01); *A61B 17/025* (2013.01); *A61B 17/2812* (2013.01); *A61B 17/8866* (2013.01); *A61B 2017/0256* (2013.01); *A61B 2017/2837* (2013.01)

(58) Field of Classification Search
USPC .............................. 606/57, 282, 90, 105, 205
See application file for complete search history.

(56) References Cited

U.S. PATENT DOCUMENTS

| | | | |
|---|---|---|---|
| 3,898,738 A | 8/1975 | Linder | |
| 6,261,296 B1* | 7/2001 | Aebi et al. | 606/90 |
| 6,663,562 B2* | 12/2003 | Chang | 600/219 |
| 6,712,825 B2 | 3/2004 | Aebi et al. | |
| 6,746,471 B2 | 6/2004 | Mortier et al. | |
| 6,764,491 B2 | 7/2004 | Frey et al. | |
| 7,060,073 B2 | 6/2006 | Frey et al. | |
| 7,625,376 B2 | 12/2009 | Brumfield et al. | |
| 2001/0047172 A1 | 11/2001 | Foley et al. | |
| 2002/0035313 A1 | 3/2002 | Scirica et al. | |
| 2002/0111537 A1 | 8/2002 | Taylor et al. | |
| 2003/0060685 A1 | 3/2003 | Houser et al. | |
| 2003/0135093 A1 | 7/2003 | Yang et al. | |
| 2008/0077156 A1* | 3/2008 | Emstad | 606/105 |
| 2009/0198240 A1* | 8/2009 | Kaufman | 606/90 |
| 2010/0016810 A1 | 1/2010 | Drews et al. | |

FOREIGN PATENT DOCUMENTS

WO  WO-DM059371  10/2001

* cited by examiner

*Primary Examiner* — Sameh Boles
(74) *Attorney, Agent, or Firm* — Gifford, Krass, Sprinkle, Anderson & Citkowski, P.C.

(57) ABSTRACT

A specialized spinous process retractor surgical instrument comprises a pair of opposing proximal handles coupled to a pair of opposing distal jaws through a joint such that when the handles are compressed the jaws spread apart, the handles defining a plane when viewed from the side. The jaws curve downwardly from the plane distally from the joint, then curve back upwardly before terminating in end portions configured for spreading. The instrument defining a centerline when viewed from above, with the jaws distally from the joint diverging outwardly from the centerline, then curving back toward the centerline before terminating in the end portions. The end portions may include opposing, outwardly facing textured or roughened bone-contacting surfaces. The end portions of the jaws when viewed from the sides may define a plane that is substantially parallel to the plane defined by the handles.

6 Claims, 3 Drawing Sheets

SPINOUS PROCESS RETRACTOR

REFERENCE TO RELATED APPLICATION

This application claims priority from U.S. Provisional Patent Application Ser. No. 61/162,416, filed Mar. 23, 2009, the entire content of which is incorporated herein by reference.

FIELD OF THE INVENTION

This invention relates generally to surgical instruments and, in particular, to an instrument which is particularly suited to spinous process retraction encountered during spine surgery.

BACKGROUND OF THE INVENTION

With the advent of artificial disc replacements and procedures such as posterior lumbar interbody fusion (PLIF) and transforaminal lumbar interbody fusion (TLIF), there is an increasing need to retract posterior spinal bony structures such as the spinous processes. Most surgeons use a laminar spreader for this purpose, but the use of this instrument has its drawbacks.

A typical laminar spreader is shown in FIG. 1. The instrument 102 has a pair of handles 104, 106 coupled to arms 114, 116 through a joint 110, such that when the handles are compressed the arms spread apart. The handles may include knurled outer gripping surfaces such as 108. The tool further includes a mechanism 122 to bias a ratchet arm 124, which engages with tip 126 of handle 104 to hold the arms 114, 116 at a desired spread until released.

The arms 114, 116 terminate flattened tips with serrated edges 118, 120. The edges are placed between adjacent lamina to spread the lamina apart. The tool 102 is typically used after spinous processes have been removed with the lamina remaining. This instrument works well for the orientation of the laminar surface but in comparison, the spinous process contact area defines a very narrow vertical surface. As such, the tool just described can slide off or cut right through the spinous process contact area. Further, the spreading arms 114, 116 also obscure the surgeon's visualization, as the tool occupies too much space in and around the spinal midline for interspinous work.

SUMMARY OF THE INVENTION

This invention resides in a specialized surgical instrument directed to spinal surgery. The instrument is particularly configured for spinous process retraction, providing a passageway facilitating access to interspinous compartments and cooperative instrument introduction. As such, the inventive instrument solves problems associated with the use of a laminar spreader of the type just described for spinous process retraction by providing a specialized tool for this such purposes.

A spinous process retractor surgical instrument according to the invention comprises a pair of opposing proximal handles coupled to a pair of opposing distal jaws through a joint such that when the handles are compressed the jaws spread apart, the handles defining a plane when viewed from the side. The jaws curve downwardly from the plane distally from the joint, then curve back upwardly before terminating in end portions configured for spreading. The instrument defining a centerline when viewed from above, with the jaws distally from the joint diverging outwardly from the centerline, then curving back toward the centerline before terminating in the end portions.

According to a preferred embodiment, the end portions include opposing, outwardly facing textured or roughened bone-contacting surfaces. The end portions of the jaws when viewed from the sides may define a plane that is substantially parallel to the plane defined by the handles. The instrument may further include a ratcheting mechanism to lock the handles and jaws in a desired spreading configuration.

DETAILED DESCRIPTION OF THE INVENTION

FIGS. 2 through 8 depict the preferred embodiment of the invention. The instrument may be constructed of any rigid material that may be sterilized, including hard plastic and/or composite materials or components, though stainless steel is used in preferred embodiment, allowing the tool to be re-used.

Figure 1:
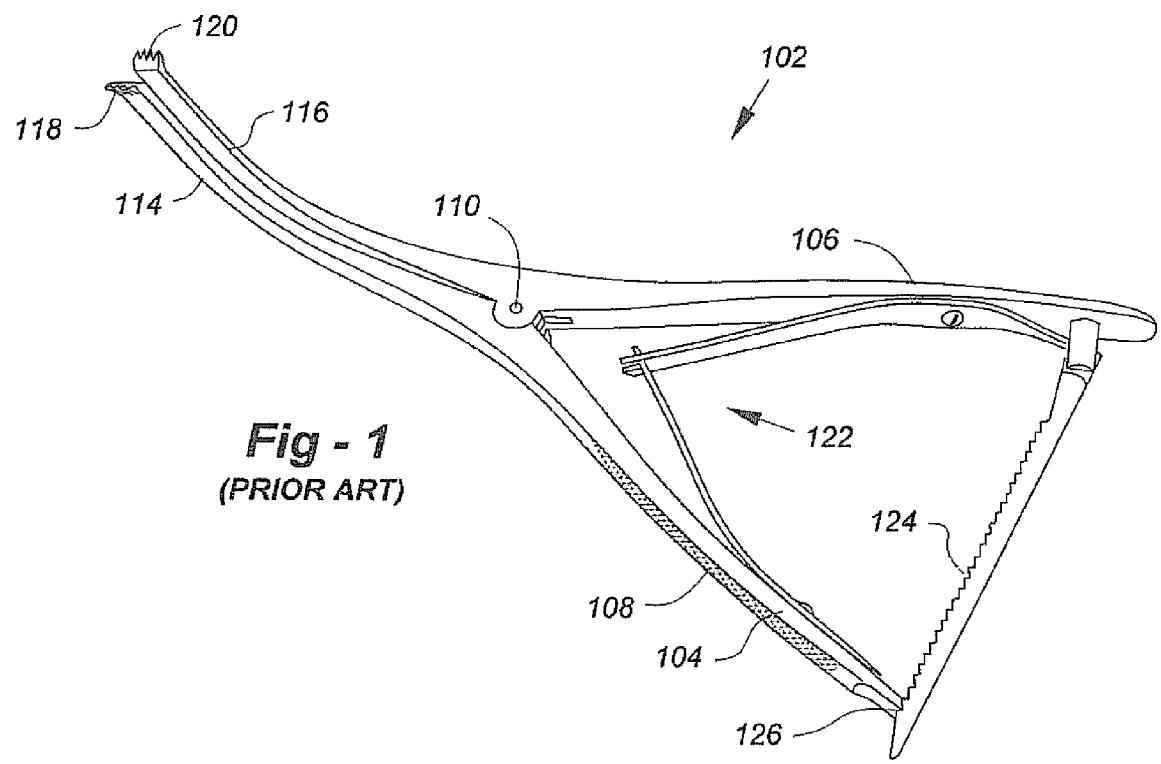
FIG. 1 is an oblique drawing of a prior art lumbar spreader.
Figure 2:
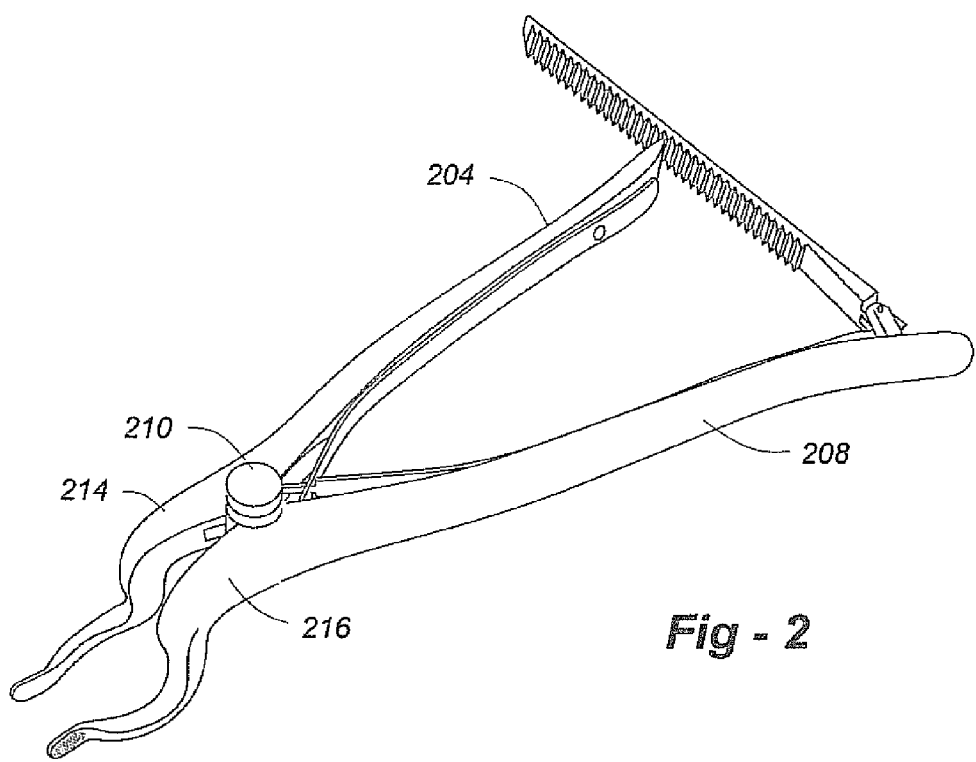
FIG. 2 is an oblique drawing of a preferred embodiment of this invention.

FIG. 2 is an oblique, perspective view. The handles 204, 208 and locking mechanism may be similar if not identical to those used with other surgical instruments, including the lumbar spreader of FIG. 1. However, forward jaws 214, 216 distal of joint 210 are unique and specialized. In addition to having a compound curve described in further detail below, the jaws terminate in flat plates with outer contact surfaces 304 to better engage with the surface of the spinous process. These surfaces are preferably textured or roughened in some manner, and may include sets of outwardly projecting points on both sides.

Figure 3:
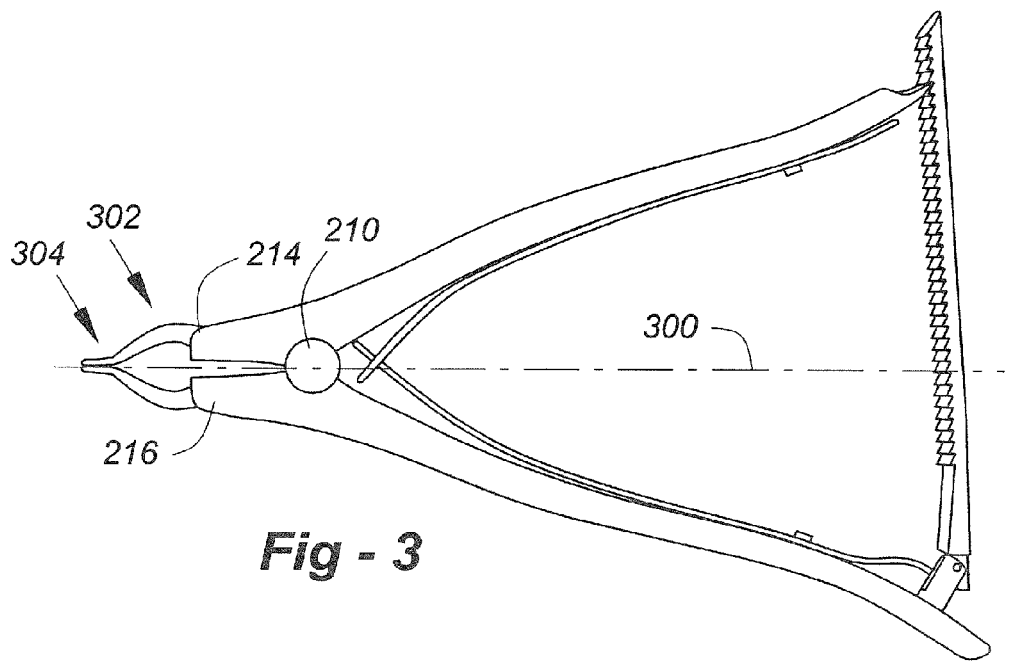
FIG. 3 is a top view of the preferred embodiment.

FIG. 3 is a top view of the instrument. Note that each jaw 214, 216 first curves away from the centerline 300, then curves back toward the centerline 300, thereby creating an opening 302 best seen from above (or below). This opening 302 establishes and maintains a passageway through which other tools can pass, such as generic tool 510 illustrated in FIG. 5.

Figure 4:
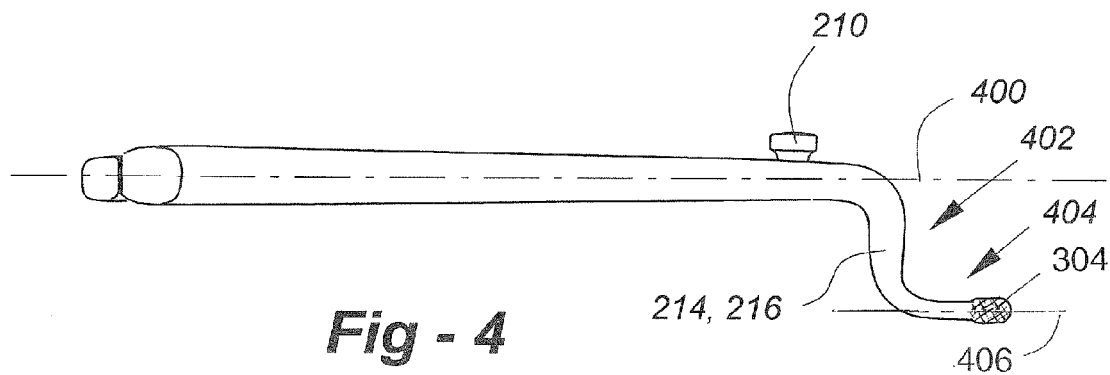
FIG. 4 is a side view of the preferred embodiment.
Figure 7:
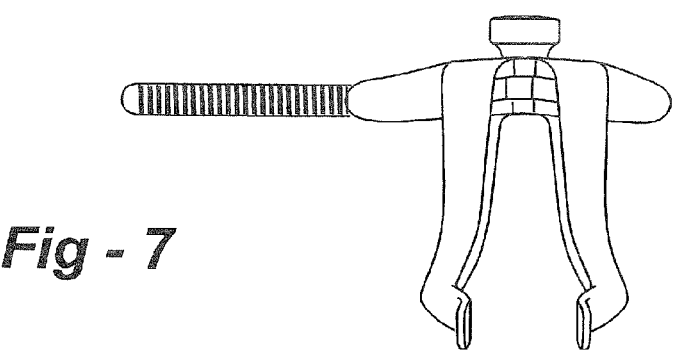
FIG. 7 is a front view of the preferred embodiment.
Figure 5:
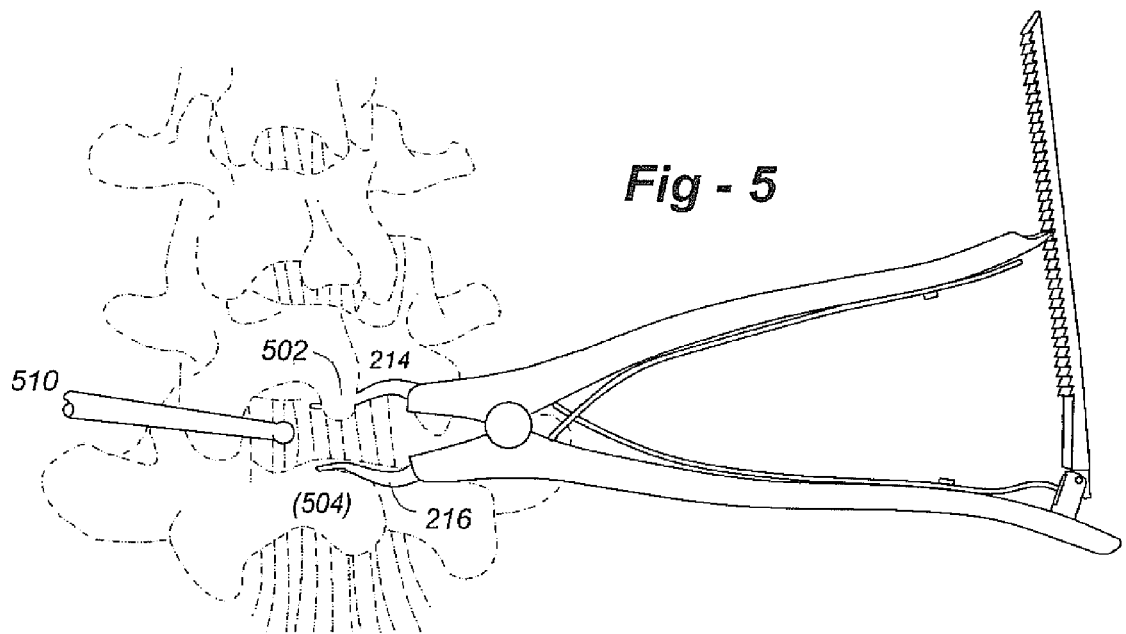
FIG. 5 is a drawing that depicts an instrument according to the invention in use.
Figure 6:
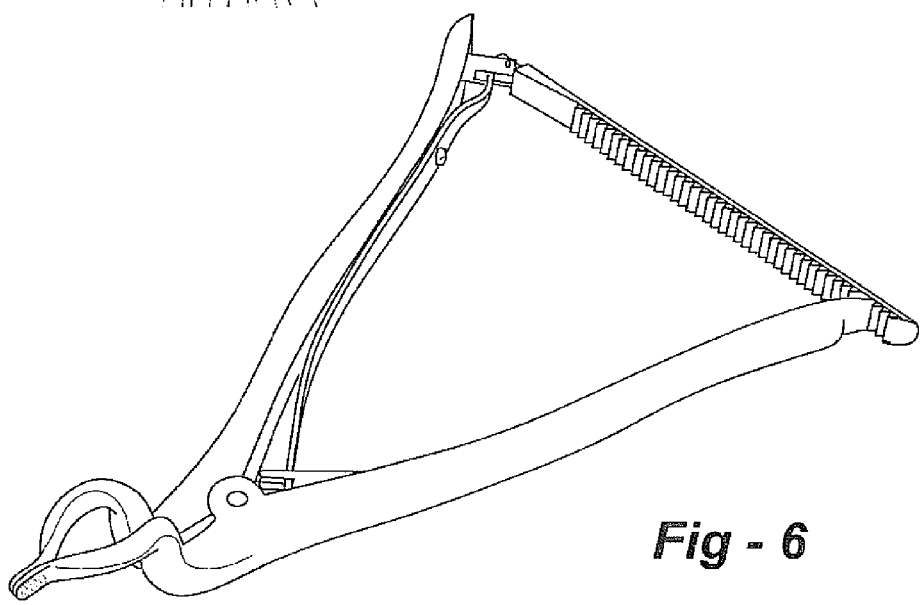
FIG. 6 is an oblique bottom view of the preferred embodiment of this invention
Figure 8:
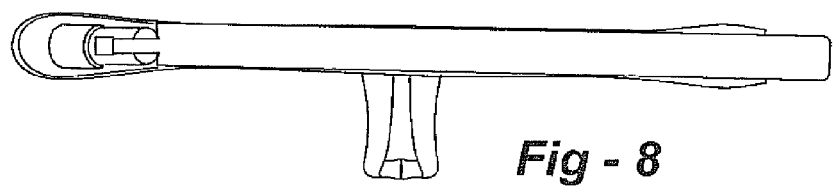
FIG. 8 is a rear view of the preferred embodiment.

FIG. 4 is a side view of the inventive instrument. In this view it can be seen that each jaw 214, 216 first curves downwardly away from the plane 400 of the handles at 402, then curves back upwardly at 404 before terminating in ends 304. Thus, as with the top view, the jaws also exhibit compound curves when viewed from the side. This 'drop' of the jaws allows the tool to remain largely out of the working channel, as depicted in FIG. 5, wherein arms 214, 216 are shown spreading spinous processes 502, 504. In the preferred embodiment, the distal ends of the jaws terminate along a plane 406 which, seen from the side, is parallel or nearly parallel to the plane 400.

I claim:

1. A spinous process retractor surgical instrument, comprising:
   a pair of opposing proximal handles coupled to a pair of opposing distal jaws through a single joint such that when the handles are compressed the jaws spread apart, the handles defining a plane when viewed from the side;
   the jaws curving downwardly from the plane distally from the joint, the jaws then curving back upwardly before terminating in end portions configured for spreading;
   the instrument defining a centerline when viewed from above, the jaws distally from the joint diverging outwardly from the centerline, then curving back toward the centerline before terminating in the end portions; and
   wherein the end portion of each jaw comprises a single flat surface that faces the single flat plate of the opposing jaw, such that the single flat surfaces contact each other when the jaws are closed; and
   wherein the end portions of the jaws further include opposing, outwardly facing textured or roughened bone-contacting surfaces.

2. The spinous process retractor of claim 1, further including a ratcheting mechanism to lock the handles and jaws in a desired spreading configuration.

3. The spinous process retractor of claim 1, wherein the end portions of the jaws when viewed from the sides define a plane that is substantially parallel to the plane defined by the handles.

4. A spinous process retractor surgical instrument, comprising:
   a pair of opposing proximal handles coupled to a pair of opposing distal jaws through a single joint such that when the handles are compressed the jaws spread apart, the handles defining a plane when viewed from the side;
   the jaws curving downwardly from the plane distally from the joint, the jaws then curving back upwardly before terminating in end portions configured for spreading;
   the instrument defining a centerline when viewed from above, the jaws distally from the joint diverging outwardly from the centerline, then curving back toward the centerline before terminating in the end portions; and
   wherein the end portion of each jaw comprises a single flat surface defining a central area, and wherein the flat surfaces, including the central areas, contact each other when the jaws are closed; and
   wherein the end portions of the jaws further include opposing, outwardly facing textured or roughened bone-contacting surfaces.

5. The spinous process retractor of claim 4, further including a ratcheting mechanism to lock the handles and jaws in a desired spreading configuration.

6. The spinous process retractor of claim 4, wherein the end portions of the jaws when viewed from the sides define a plane that is substantially parallel to the plane defined by the handles.

\* \* \* \* \*